United States Patent [19]

Newton

[11] Patent Number: 4,714,464
[45] Date of Patent: Dec. 22, 1987

[54] MECHANISM FOR COUPLING THE ASPIRANT LINE OF AN IRRIGATION/ASPIRATION MACHINE TO THE PRESSURE MONITORING SECTION

[75] Inventor: Walter A. Newton, Lenoir, N.C.

[73] Assignee: Entravision, Inc., Lenoir, N.C.

[21] Appl. No.: 923,277

[22] Filed: Oct. 27, 1986

[51] Int. Cl.⁴ ............................................. A61M 5/00
[52] U.S. Cl. ...................................... 604/118; 604/30
[58] Field of Search ................... 604/22, 30, 35, 118, 604/119; 433/27, 98; 417/422

[56] References Cited

U.S. PATENT DOCUMENTS

| | | | |
|---|---|---|---|
| 4,184,510 | 1/1980 | Murry et al. | 604/22 |
| 4,493,695 | 1/1985 | Cook | 604/30 |
| 4,560,144 | 12/1985 | Williams et al. | 604/119 |
| 4,661,093 | 4/1987 | Beck et al. | 604/119 |

Primary Examiner—John D. Yasko
Assistant Examiner—J. L. Kruter
Attorney, Agent, or Firm—Charles R. Rhodes; Judith E. Garmon

[57] ABSTRACT

A linking mechanism for irrigation/aspiration machines which includes a coupling member having a plug that is inserted into an opening in a receptacle on the face of the I/A machine. The plug projection is sealed in air tight relation to the wall surrounding the opening and an auxiliary prong(s) prevent rotation of the plug as well as lock the plug in the receptacle. The receptacle includes an arming switch activated responsive to proper seating of the plug in the receptacle to arm the peristaltic pump that is subsequently operated by a foot switch to generate a vacuum in the aspirant line.

8 Claims, 4 Drawing Figures

MECHANISM FOR COUPLING THE ASPIRANT LINE OF AN IRRIGATION/ASPIRATION MACHINE TO THE PRESSURE MONITORING SECTION

BACKGROUND AND SUMMARY OF THE PRESENT INVENTION

This application is related to an improvement in the control of an aspirant line (sometimes referred to as the fluid flow system) in a surgical irrigation/aspiration (I/A) machine of the type used for supplying irrigation solution to operative sites (generally the eye) and removing such infusion liquids and macerated tissue therefrom. In such surgical machines it is critical that the pressure at the operative site be maintained at relatively constant limits, particularly where the total volume within the operative site is small in relation to the rest of the fluid in the system. Such surgical devices are generally described in U.S. Pat. Nos. 3,589,363; 3,693,613; and 3,902,495; and in applicant's own pending application Ser. No. 674,064, filed Nov. 14, 1984 and application Ser. No. 647,818, filed Sept. 6, 1984.

The previously mentioned patents and applications describe irrigation/aspiration machines which are used in conjunction with a surgical handpiece. The hand instrument of such machines either cuts or ultrasonically breaks apart unwanted tissue and material, while simultaneously introducing an irrigant into the eye chamber and withdrawing excess fluid and macerated tissue. Treatment or irrigation fluid is introduced into the operative site at a constant low pressure. This introduction of irrigating fluid is to provide a replacement for the fluids which are withdrawn or lost from the operative site such as the eye chamber. The withdrawal of fluid and suspended materials from the operative site is called aspiration, and under ideal conditions and procedures, there is no change in the fluid or chamber pressure as a result of this irrigation/aspiration procedure. Realistically, however, it is impossible to achieve an ideal constant pressure at the operative site since the aspiration procedure is intended to remove solid materials which sometimes occlude or block the fluid withdrawal openings of the surgical handpiece. Some of the problems with control of fluid content and pressure within the operative site during the use of irrigation/aspiration procedures is discussed in detail in the aforementioned U.S. Pat. No. 3,693,613, issued Sept. 26, 1972 to Charles Kelman for a surgical handpiece and flow control system for use therewith. As explained in this patent, when the surgical handpiece is inserted into the operative site, it is very important that the pressure within the operative site be maintained within a certain range of values. If the pressure is not maintained at a prescribed level, parts of the operative site, such as the eye, can be damaged.

To aid in controlling this critical pressure, it has become customary to provide a pressure monitoring section in the I/A machine which continuously senses the vacuum in the aspirant line. When the vacuum exceeds a prescribed limit, a vent valve is opened to the atmosphere to reduce the vacuum in the aspirant line. For example, the aspiration sub-system most frequently comprises a peristaltic aspiration pump used to withdraw the aspirant through a tube or line, an intermediate point of which is interconnected to the pressure monitoring section of the I/A machine. The monitoring section responds to pressure changes in the aspirant line by sending some type of signal to the vent valve which responds by opening the aspirant line to the atmosphere. The function of the vent valve is to provide for pressure equalization between atmospheric pressure and the hydraulic pressure in the fluid flow system. This equalization function is commonly referred to as "venting", and negates a vacuum buildup in the aspiration line. The peristaltic pump is operated by the surgeon by use of a foot switch or pedal normally having an "off" position, multiple "on" positions, and a "transition" position. Disposable surgical irrigation/aspitation set-up kits are provided to the surgical team for selectively connecting the irrigation/aspiration machine to: (1) the hand instrument being used by the surgeon, (2) to the sterile fluids being used for irrigation, and (3) through the peristaltic pump to the disposable receptacle which received these fluids and tissues as they are aspirated from the operative site. A new setup kit is provided with each surgical operation and is disposed of after the surgery is performed. Applicant's previously mentioned pending applications are directed in part to such set-up kits, as is U.S. Pat. No. 4,418,944 to Haines et al, wherein a set-up kit is disclosed which includes a disposable, releasable connector called a "cam lock tee".

The Haines connector is affixed to the aspiration tubing and is snapped into place in a corresponding receptacle on the front of the irrigation/aspiration machine. This connector has an air passageway longitudinally therethrough and a branch thereof which leads from the longitudinal air passageway through an opening on the side of the connector. The opening mates with a corresponding opening in the receptacle on the face of the I/A machine leading to the vent valve and its associated monitoring equipment within the machine. When the connector is properly seated there is direct communication between the aspiration line and the interior of the irrigation/aspiration machine whereby the critical air pressure (vacuum) within the aspiration line may be monitored.

In the Haines et al connector, as in the connector described in applicant's previously filed pending applications, proper seating of the connector in the front panel receptacle is critical. Rather than being simply inserted directly into an opening on the front panel, some type of rotating and locking of the connector has been required. Because of the peculiar shape of the connector and the transverse air passageway, proper seating of the connector and reliable alignment of the branch line and the air passageway into the machine have been difficult at best. Additionally, there are problems in creating a tight seal between the connector and the entrance in the receptacle to the machine air passageway to prevent a loss of vacuum in the aspiration line. It previously has been believed that the peculiar shape and use of a connector or coupling device such as the previously known "cam lock tee" has been necessary to ensure that there is no displacement or rotation of the coupling during a surgical procedure. Any such displacement or rotation not only threatens the seal, but also may detrimentally effect the operation of the pump. It is also important that the aspirant line remain horizontal to the extent possible to promote proper aspirant flow. The loss of vacuum resulting from poor sealing of the connector or improper alignment of the aspirant line leading to the peristaltic pump are the primary problems in the use of existing disposable set-up kits. It was therefore to the improvement of the coupling of the aspirant tubing to the irrigation/aspiration machine, and to the overcoming of all of the above discussed problems, that the present inventor turned during the development of the invention disclosed herein.

SUMMARY OF THE PRESENT INVENTION

The present inventor has developed an improved coupling means for connecting the tubing set-up to the venting receptacle. The improved coupling further includes a safety arming switch for the peristaltic pump circuit. The improved coupling provides for a direct, straight line, reliably sealed connection between the entrance to the vacuum monitoring air passageway and the aspirant tubing of the fluid flow control sub-system. Further, should the coupling not be completely seated to effect the seal or should the coupling become inadvertently displaced, the vacuum pump is deactivated.

In the past, if the aforementioned displacement of the coupling occurred during surgery, proper operation of the aspirant removal and/or the vacuum monitoring function could be interrupted without the knowledge of the operating physician. In such instances, the physician could continue surgery and operation of the peristaltic pump without being aware that the vacuum in the aspiration line was leaking and/or the monitoring function was inoperative to control the critical negative pressure in the aspiration line. The applicant's present invention in the improved coupling and receptacle leading to the pressure monitoring components eliminates this problem by including a means whereby displacement of the coupling automatically deactivates the peristaltic pump.

The coupling device itself includes a locking feature, as well as a plurality of sealing rings which ensure a tight seal in the connection between the air passageway leading to the pressure monitoring components and the air passageway from the aspirant line through the coupling.

In a preferred embodiment the coupling itself includes a hydrophobic filter, all of which is disposable along with the disposable aspirant tubing after each surgical procedure.

It is therefore a primary object of this invention to provide an improved machine used in irrigating and aspirating a surgical site.

Another object of the present invention is the provision of an improved coupling means for quickly and reliably connecting the air passageway leading from the aspirant tubing or fluid flow sub-system to the pressure monitoring section of the machine.

Yet another object of the present invention is to provide an improved I/A machine of the type described in which the peristaltic pump circuit is not armed unless the aspirant line connector is properly seated in the pressure monitoring receptacle.

Other objects and advantages of the present invention will become apparent to those skilled in the art when the following detailed description of a preferred embodiment is studied in conjunction with the accompanying drawings.

A BRIEF DESCRIPTION OF THE DRAWINGS

DETAILED DESCRIPTION OF A PREFERRED EMBODIMENT

Figure 1:
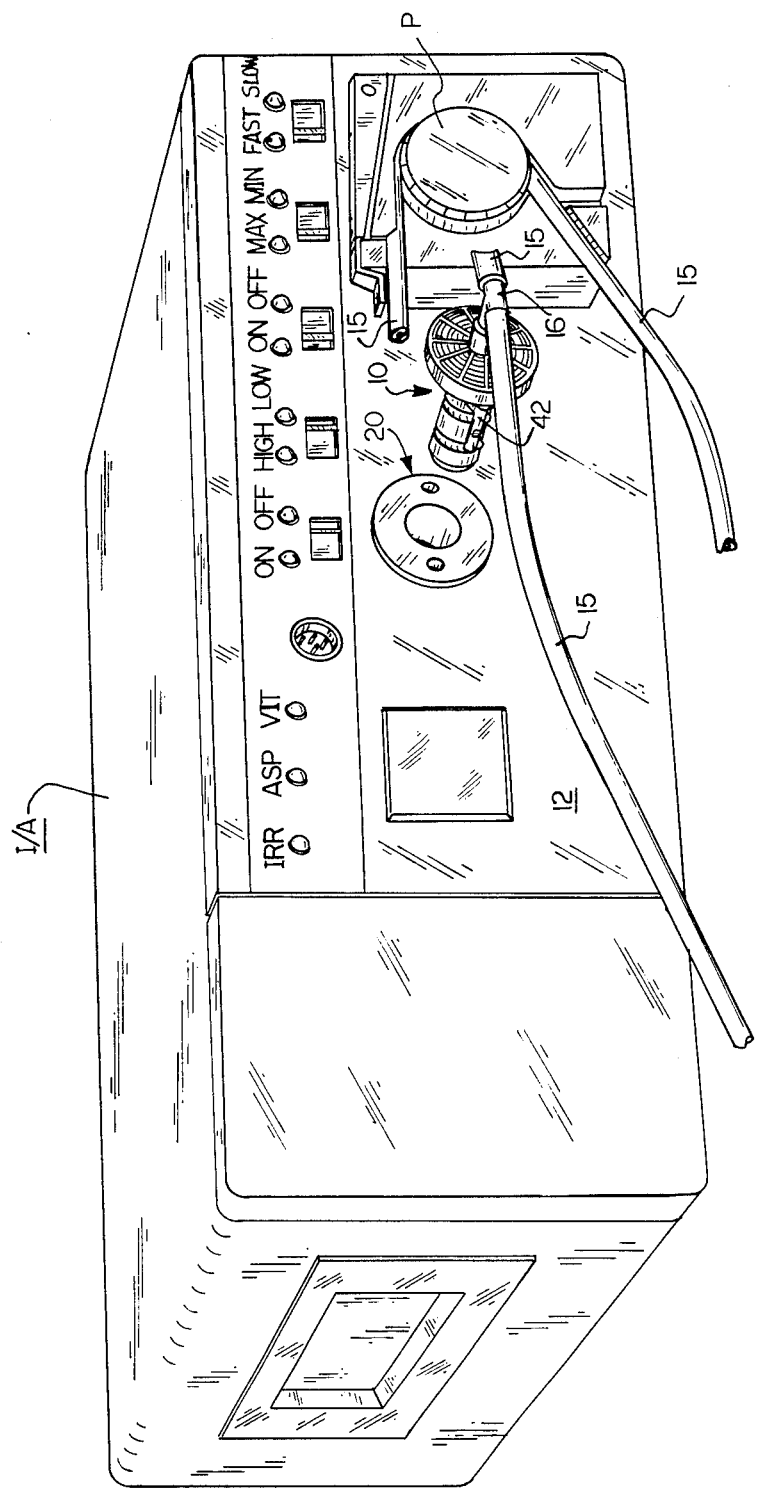
FIG. 1 is a perspective view of the front panel of the irrigation/aspiration machine showing its basic external construction and connections to the aspirant line control sub-system, it being understood that the irrigation line, the handpiece, and the foot pedal are not shown.
Figure 2:
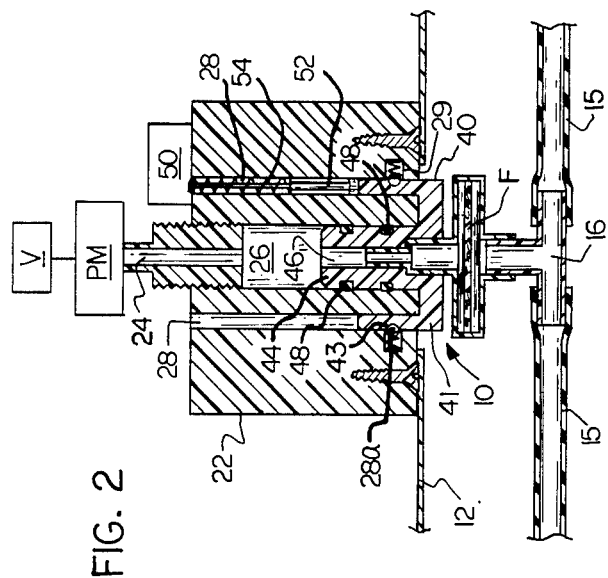
FIG. 2 is a cross-sectional plan view of the connection between the improved connector and receptacle.
Figure 3:
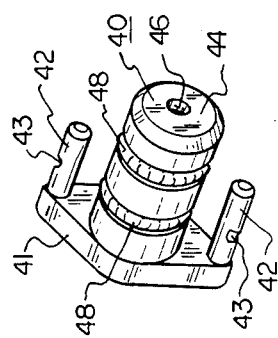
FIG. 3 is a perspective view of the improved coupling device or connector.

Looking first at FIG. 1 the irrigation/aspiration machine (I/A machine) of the present invention is shown with the coupling device or connector 10 and attached I/A aspirant tubing 15. The coupling 10 plugs into a receptacle 20 leading to the vacuum monitoring section PM of the I/A machine as will be described in detail below. The peristaltic pump P controls the flow of the aspiration fluid generally by means of a foot pedal control switch operated by the surgeon. At the outset, a branch line is established between the aspirant tubing 15 and receptacle 20 by interposing a T-shaped tubular member 16 in the aspirant tubing 15 as illustrated in FIG. 2. The coupling device 10 then connects the perpendicular leg of the T-shaped tubular member to the receptacle 20.

FIG. 2 is a cross-sectional plan view illustrating the relationship of the receptacle 20 having seated therein the coupling element 10. The receptacle 20 includes a body member 22 that is suitably mounted inside the front panel 12 of the I/A machine. Body member 22 includes a central opening or air passageway 26 therein that is connected to the pressure monitoring section PM and vent valve V by means of an air line that also opens responsive to a signal generated by the pressure monitoring section PM to increase the pressure in line 15. Returning now to a description of the receptacle 20, a pair of guide channels 28 spaced on either side of the air passageway 26 extend parallel to the passageway 26 through the body member 22. These channels receive the prongs 42 of the coupling element 10 as described hereinbelow.

The coupling element 10 shown in FIGS. 1 and 2 primarily includes a plug 40 which is connected to the tubular member 16 either directly or with a hydrophobic filter F interposed therein. The hydrophobic filter F preferably includes a filter media of such make-up as to prevent the passage of bacterial liquid aspirant, and microorganisms as explained in applicant's co-pending patent application Ser. No. 674,064, filed Nov. 19, 1984. Plug 40 includes a central projection 44 extending rearwardly from body portion 41. The aforesaid prongs 42 also project rearwardly from portion 41 into the guide channels 28 as described above. The central projection 44 is inserted in air passageway 26 and which includes its own air passageway 46 therethrough. Plug passageway 46 and receptacle passageway 26, when connected, provide a direct air line to the pressure monitoring section PM and vent valve V from the aspiration tubing 15. Two O-rings 48 around the central projection seal against the adjacent wall of passageway 26 ensure an air tight fit therebetween and prevent loss of air from passageway 26 around the outside of projection 44. The prongs 42 each include an indention 43 along the surface thereof to lock the plug member 40 with the receptacle.

For this purpose the passageways 28 each include a spring biased retaining ball 28a in an adjacent recess 29 in the wall surrounding passageway 28. Further, the receptacle 20 includes an arming switch 50 attached thereto in operative communication with one of the passageways 28. A spring biased plunger 52 is positioned in the passageway 28 in the path of prong 42 of the plug 40. Spring 54 normally biases the plunger forwardly to a position ahead of the innermost position of the end of prong 42. The arming switch 50 is connected to a microprocessor 60, and unless tripped, the arming switch will not allow activation of pump P.

The parallel side prongs 42 which are inserted into channels 28 also prevent rotation of the coupling member 40, and thus ensure alignment of the aspirant tubing 15 with the entrance to pump P. This is important to keep kinks out of the tubing and maintain it at a horizontal attitude adjacent the entrance to pump P.

A foot pedal (FIG. 4) normally controls the peristaltic pump to aspirate fluid from the operative site. In prior art situations when the coupling between the disposable aspirant tubing and the receptacle is not secure the pump P continues to function regardless of the vacuum pressure in line 15. This can either cause loss of vacuum or result in improper pressure monitoring. In such situations it is thus possible for the peristaltic pump to be activated and to increase the critical pressure without the surgeon's immediate knowledge. The present invention overcomes this problem in that the microprocessor 60 will not allow initiation of the peristaltic pump if the arming switch 50 is not activated, even if the foot pedal switch is activated. Therefore, if the plug 40 is not completely seated (which ensures a proper seal), the pump cannot be activated. Arming switch 50 is tripped or activated by the plunger mechanism 52 that is spring biased into a normally "off" condition, out of engagement with the pressure responsive arming switch 50. When the coupling member 40 is properly inserted into the vent receptacle and prongs 42 into channels 28, one of the prongs 42 activates or compresses the plunger 52 to engage and activate the arming switch 50. Therefore, if the coupling device is not properly coupled into the vent receptacle 22, the arming switch 50 cannot be activated to turn on the secondary switch to the foot pedal which controls the peristaltic pump.

Figure 4:
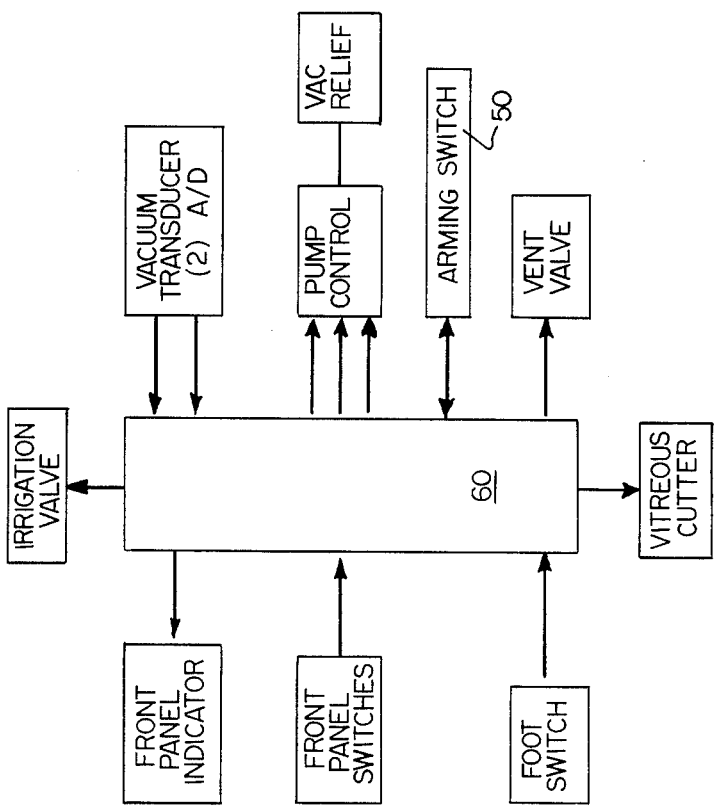
FIG. 4 is a block diagram schematically illustrating the operative relationship between the various switch, controls, handpiece, valves, the peristaltic pump, and the microprocessor.

The operative relationship of the above components is illustrated in FIG. 4. There it is shown that a microprocessor 60 receives and processes signals from the pressure sensors, fluid flow monitors, etc. The preferred microprocessor is model HD63705 made by Hitachi, and equivalent to model 6805 by Motorola Corporation. When the I/A machine is readied for surgery, the coupling prong 42 depresses plunger 52 to actuate the arming switch 50 (FIG. 2). If during surgery the coupling is interrupted, the arming switch is deactivated, resulting in a signal to the microprocessor to turn off or deactivate the peristaltic pump. Therefore, the pump cannot operate when the aspirant line 15 is not properly coupled to the vent valve V.

While a preferred embodiment has been described above, it is recognized that other and further modification might be made by those skilled in the art while remaining within the scope of the claims below.

What is claimed is:

1. A safety machanism for irrigation/aspiration machines of the type which include a peristaltic pump producing a vacuum in an aspirant line and which machines include a vacuum monitoring section for sampling the pressure in said aspirant line, said safety mechanism comprising:
   (a) a receptacle on said machine having a passageway through which said air samples pass and having an arming switch with "on" and "off" positions, said peristaltic pump being armed responsive to the activation of said arming swtich;
   (b) a coupling means seatable in said receptacle in sealed relationship thereto for connecting said aspirant line to said vacuum monitoring section;
   (c) said coupling means further including a means for activating said arming switch when said coupling is fully seated on said receptacle in said sealed relationship;

whereby, upon improper seating of said coupling means, said arming switch is deactivated and said pump is deactivated.

2. The mechanism according to claim 1 wherein said coupling means includes:
   (a) a plug member having a central projection extending therefrom for insertion into said receptacle on the irrigation/aspiration machine; said plug including an air passageway through said projection registrable with the passageway in said receptacle for delivery of air from said aspirant tubing to said pressure monitoring section; and
   (b) said central projection including a sealing means around the periphery thereof engagable with the wall of said passageway to form an air seal therebetween.

3. The mechanism according to claim 2 wherein said coupling means further includes at least one prong member extending in parallel relationship to said central projection into a corresponding channel in said receptacle, locking means associated with said prong member and said corresponding channel for preventing inadvertent removal of said plug member.

4. The mechanism according to claim 3 wherein said locking means comprises an indent in said prong member and a spring biased locking member seated in said receptacle adjacent the wall of said channel, said locking member being biased toward engagement with the indent in said prong when seated.

5. The mechanism according to claim 4 wherein said means for activating said arming switch compmises:
   (a) a plunger means mounted in said channel in the path of said prong member for operatively engaging said arming switch when said coupling means is properly seated in said receptacle;
   (b) spring means in said channel connecting said plunger and said arming switch for normally biasing said plunger in a position out of operative engagement with said arming switch;
   (c) said plunger means overcoming said spring means and being moved into operative engagement with said switch means responsive to seating of said plug member.

6. A linking mechanism for irrigation/aspiration machines of the type which includes a peristaltic pump producing a vacuum in an aspirant line leading from a surgical site, and which machines include a vacuum monitoring section therein for continuously sampling the pressure (vacuum) in said aspirant line, wherein said linking mechanism joins a branch from the aspirant line to said vacuum monitoring section and comprises:
   (a) a receptacle on the face of said machine and a coupling member selectively seated in said receptacle;
   (b) said receptacle including
      (i) a first air passageway therethrough open at both ends and extending through said receptacle, said air passageway having an outlet connected to said pressure monitoring section for passage of air from said receptacle housing thereto, and an inlet through which sampled air from said aspirant line is received;

(ii) at least one channel means extending through said receptacle housing parallel to said air passageway and having a locking means therein;

(c) said coupling member receiving said branch from said aspirant line and including a plug having a central projection extending therefrom for insertion into said air passageway in said receptacle, said central projection including an air passageway therethrough registrable with said air passageway in said receptacle for communication with said aspirant line, said central projection including a sealing means around the periphery thereof engageable with the wall surrounding the air passageway in said receptacle to form an air seal therebetween.

7. The linking mechanism according to claim 6 wherein said plug further includes at least one prong member extending in parallel relationship to said central projection into a corresponding channel in said receptacle, locking means associated with said prong member and said corresponding channel for preventing inadvertent removal of said plug member.

8. The linking mechanism according to claim 5 wherein said locking means comprises an indent in said prong member and a spring biased locking member seated in said receptacle adjacent the wall of said channel, said locking member being biased toward engagement with the indent in said prong when seated.

* * * * *